United States Patent
Stedman et al.

(10) Patent No.: US 9,227,030 B2
(45) Date of Patent: Jan. 5, 2016

(54) ENHANCED EDUCTOR DESIGN

(75) Inventors: Benjamin Stedman, San Jose, CA (US); Prashant Kakade, Mountain View, CA (US); Darrell Woehler, Apache Junction, AZ (US); John Leonard, Mesa, AZ (US)

(73) Assignee: MAP Pharmaceuticals, Inc., Irvine, CA (US)

( * ) Notice: Subject to any disclaimer, the term of this patent is extended or adjusted under 35 U.S.C. 154(b) by 753 days.

(21) Appl. No.: 12/978,254

(22) Filed: Dec. 23, 2010

(65) Prior Publication Data
US 2011/0155129 A1 Jun. 30, 2011

Related U.S. Application Data

(60) Provisional application No. 61/284,784, filed on Dec. 23, 2009.

(51) Int. Cl.
*A61M 15/00* (2006.01)
*F15D 1/02* (2006.01)

(52) U.S. Cl.
CPC ......... *A61M 15/0091* (2013.01); *A61M 15/009* (2013.01); *A61M 15/0026* (2013.01); *F15D 1/02* (2013.01); *A61M 2206/16* (2013.01)

(58) Field of Classification Search
CPC ... A61M 11/00; A61M 11/006; A61M 15/00; A61M 15/0001; A61M 15/0005; A61M 15/0006; A61M 15/0008; A61M 15/002; A61M 15/0086; A61M 15/0091; A61M 15/0095; A61M 16/00; A61M 16/0003; A61M 16/0015; A61M 16/0018

USPC ............. 128/200.14, 200.23, 200.24, 203.12
See application file for complete search history.

(56) References Cited

U.S. PATENT DOCUMENTS

| | | | |
|---|---|---|---|
| 2,037,940 A | 4/1936 | Stalker | |
| 3,665,949 A | 5/1972 | Rivard | |
| 4,046,146 A | 9/1977 | Rosskamp | |
| 4,127,123 A * | 11/1978 | Bird .......................... | 128/204.25 |
| 5,036,847 A * | 8/1991 | Boussignac et al. ..... | 128/207.14 |
| 5,161,524 A | 11/1992 | Evans | |
| 5,415,162 A | 5/1995 | Casper | |
| 5,657,749 A | 8/1997 | Cox | |
| 5,740,794 A | 4/1998 | Smith et al. | |
| 5,826,570 A | 10/1998 | Goodman et al. | |
| 5,954,047 A | 9/1999 | Armer et al. | |

(Continued)

FOREIGN PATENT DOCUMENTS

| | | |
|---|---|---|
| DE | 2031880 | 1/1971 |
| WO | WO0166064 A2 | 9/2001 |

OTHER PUBLICATIONS

International Search Report mailed on Mar. 7, 2011, for PCT Patent Application No. PCT/US2010/62084, filed on Dec. 23, 2010, 4 pages.

(Continued)

*Primary Examiner* — Rachel Young
(74) *Attorney, Agent, or Firm* — Barbara C. Potts

(57) ABSTRACT

The present invention provides for an enhanced eductor element that significantly increases the amount of pressure generated at the siphon tube without significantly increasing the flow resistance through the eductor. The invention further provides for breath-actuated inhalation devices comprising the enhanced eductor element as an actuation mechanism.

19 Claims, 10 Drawing Sheets

(56) References Cited

U.S. PATENT DOCUMENTS

Figure 1:
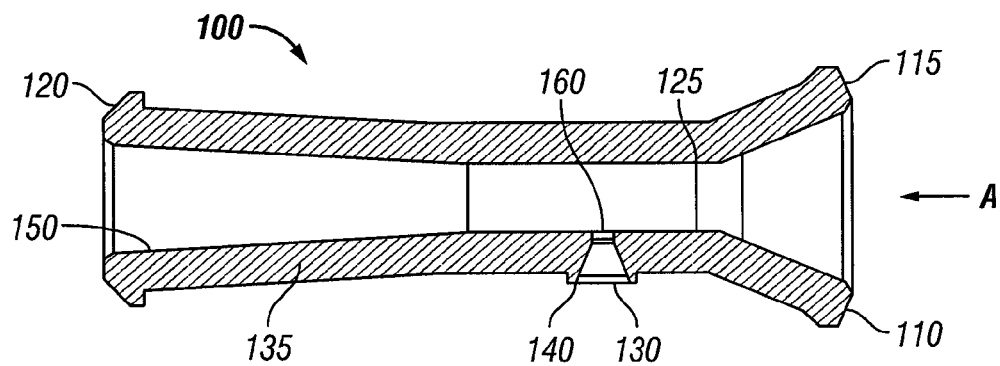
Figure 2:
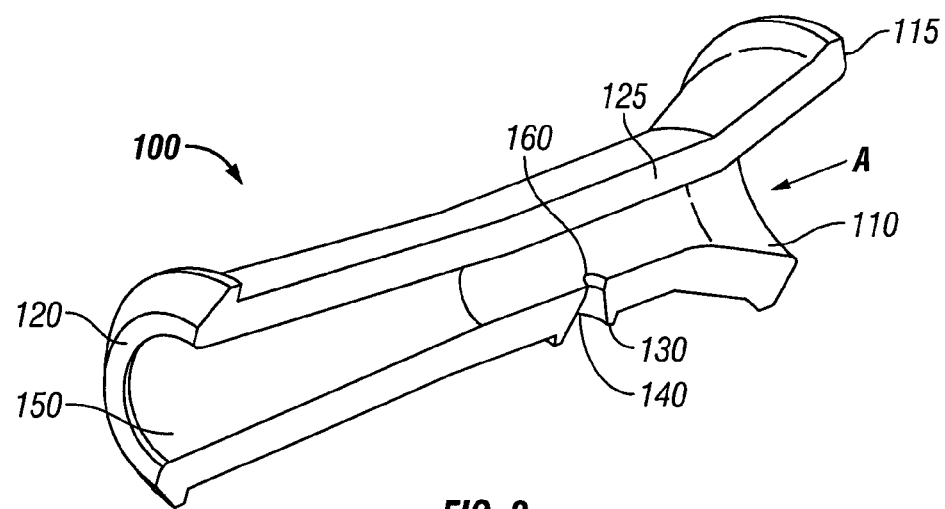
Figure 3:
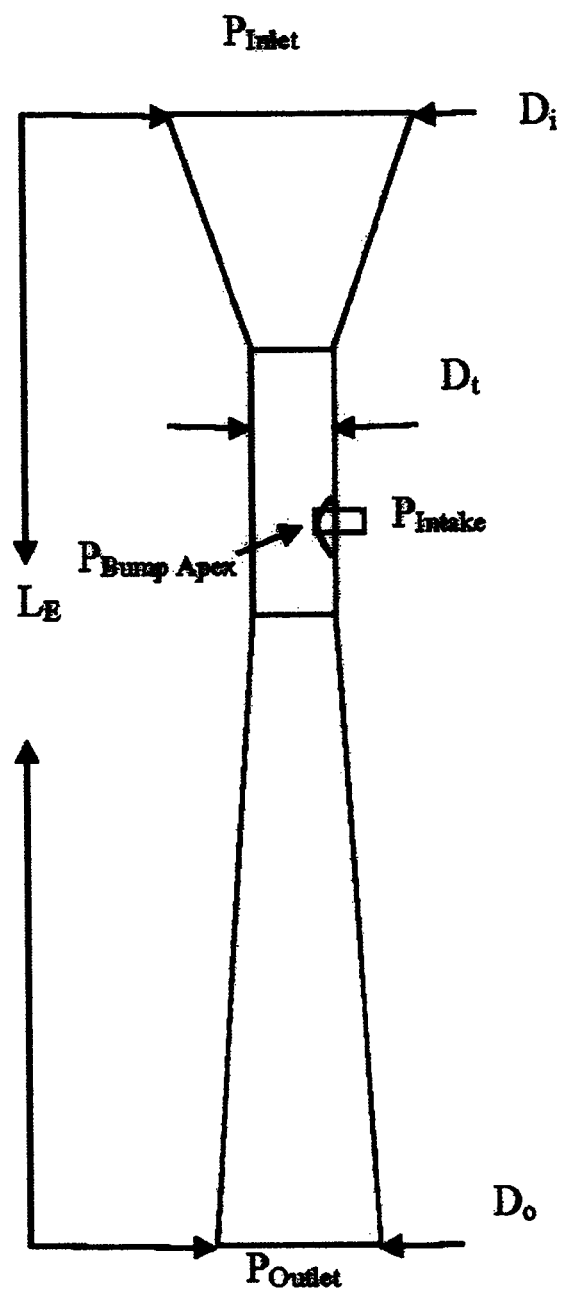

| | | | |
|---|---|---|---|
| 6,026,808 | A | 2/2000 | Armer et al. |
| 6,905,141 | B2 | 6/2005 | Winter et al. |
| 6,948,496 | B2 | 9/2005 | Eason et al. |
| 2004/0011357 | A1 | 1/2004 | Braithwaite |
| 2004/0069303 | A1 | 4/2004 | Brown et al. |

OTHER PUBLICATIONS

Written Opinion mailed on Mar. 7, 2011, for PCT Patent Application No. PCT/US2010/62084, filed on Dec. 23, 2010, 5 pages.

Supplementary EU Search Report, European Applkcation No. 10840198.5, Feb. 4, 2015, pp. 5., European Patent Office, EP.

* cited by examiner

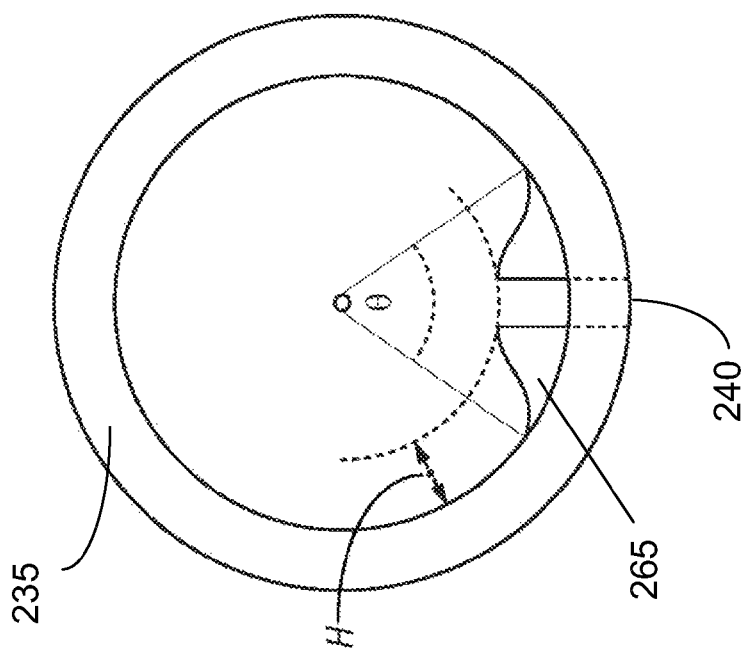
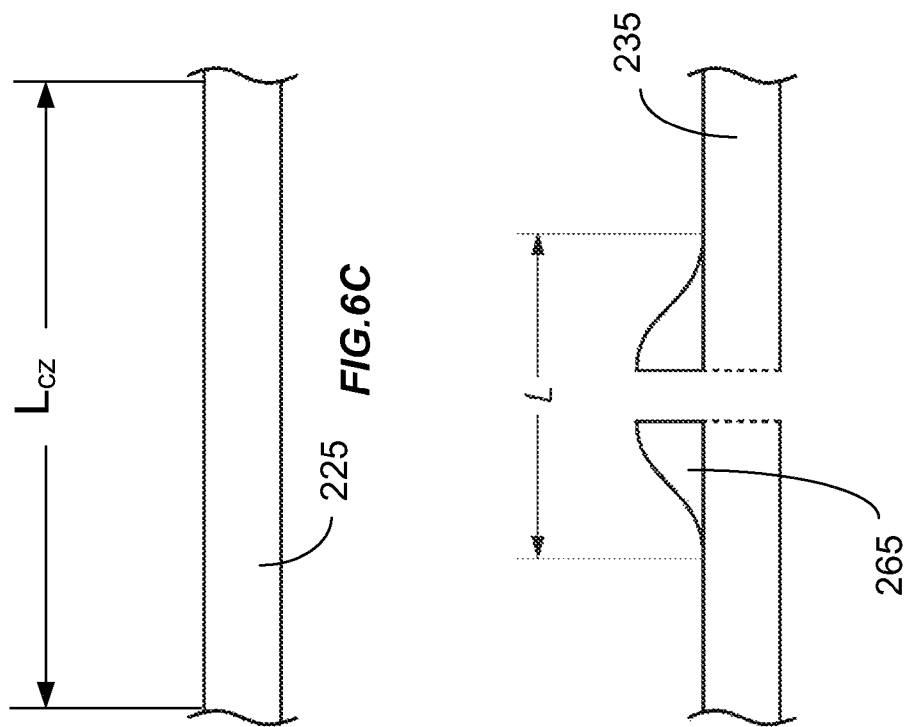

ENHANCED EDUCTOR DESIGN

CROSS REFERENCE TO RELATED APPLICATIONS

This application claims the benefit of U.S. Provisional Application No. 61/284,784, filed 23 Dec. 2009, entitled "Enhanced Eductor Design" which is hereby incorporated by reference in its entirety.

FIELD OF THE INVENTION

This present invention relates to metered dose inhaler devices and elements thereof for use in delivery of particulate medicaments by oral inhalation, and in particular to eductor elements having enhanced performance and breath-actuated pressurized metered dose inhalers that employ such enhanced eductors to increase siphon pressure drop while minimizing increased pressure drop over a range of operating flow rates.

BACKGROUND OF THE INVENTION

For many years, oral inhalation delivery of drug-laden aerosols to the lungs has been an effective means of drug delivery. One type of device that is effective for delivering particulate drugs is a metered dose inhaler, which includes a pressurized canister with a metering valve that contains a drug formulation. In "press and breathe" versions of metered dose inhalers, the canister is placed within an actuator comprised of a housing that covers a lower portion of the canister, leaving the top portion exposed. The metering valve seats into a sump/orifice assembly inside the base of the housing. The orifice is positioned at an acute angle to the valve stem and directs discharge of the particulate drug formulation approximately through a conduit attached to the housing at a 90 degree angle and terminating in a mouthpiece. To administer the drug, the user seals his/her lips around the mouthpiece of the device and simultaneously inhales (an inspiratory breath) while depressing the exposed portion of the canister into the housing. The canister translates downward in a manner which actuates the metering valve and thus causes release of the drug as an aerosol plume which is then drawn into the respiratory tract as the user inhales. It can be difficult for some users to coordinate the release of the aerosol plume with their inspiratory breath.

In order to address problems with "press and breathe" actuated inhalers, improved inhaler devices have been developed that release the aerosol plume of drug automatically when the user takes in an inspiratory breath. These are termed "breath-actuated pressurized meter dose inhalers" ("BApMDI"s). In exemplary BApMDI devices, actuation can be carried out using a spring that is compressed by opening a cover. This spring energy is stored until the BApMDI is triggered by the user's breath, at which time the spring force is applied to depress the pressurized canister and cause the release of a plume of aerosolized medication into the users' breath. Such triggering mechanisms depend upon an eductor element that includes a venturi having a flow path that narrows in a constriction zone and serves to increase the local velocity of the flow of inspiratory breath to create a siphon suitable to actuate the device.

Although BApMDI devices represent an improvement in the art, it has been found that the energy (pressure drop) required to trigger the spring energy (and thus actuate the device) may exceed that which can be applied by a normal human breath. This can particularly present a problem where the user has compromised lung function, or where the user is an adolescent without the lung capacity of an adult. There accordingly remains a need in the art to provide improved BApMDI devices with a triggering mechanism that enables actuation with a normal human breath.

SUMMARY OF THE INVENTION

It is an object of the invention to provide an enhanced eductor element having improved performance characteristics. The invention arises from the discovery that introduction of a protrusion or structure into the constriction zone surrounding the inlet apex of the siphon of a conventional eductor significantly increases the siphon pressure drop as a function of flow rate, without significantly increasing the pressure drop across the eductor. This was unexpected and contrary to existing knowledge in the art that inclusion of any structure or modification member along the interior wall of the hollow bore of an eductor may help increase the siphon pressure drop of that element, however, it would also result in higher pressure drop across the eductor and thus harm the performance of the modified eductor. The enhanced eductor of the present invention can be used to reduce the inspiratory flow rate needed to trigger a breath-actuated inhaler device and therefore facilitate orally inhaled medicament delivery for younger patients and for those patients with compromised lung function.

In one aspect of the invention, an enhanced eductor element is provided that includes: (a) a conduit with an inlet and an outlet; (b) an outer surface and an inner surface, where the inner surface forms a hollow bore that extends from the inlet to the outlet and is a generally smooth and continuous curvilinear surface; (c) a constriction zone that is formed by a reduction in the diameter of a portion of the hollow bore at a location that is between the inlet and the outlet, where the constriction zone has a smaller diameter than the diameter of the main inlet and the outlet; (d) a modification member that is positioned upon the inner surface hollow bore and in the constriction zone, wherein the modification member is a structure or protrusion that locally reduces the diameter and cross-sectional area of the constriction zone; and (e) a siphon channel that establishes fluid communication between the outer surface of the eductor and the inner surface of the hollow bore through such channel, where the channel is positioned adjacent to, or surrounded by the modification member.

In some variations, the enhanced eductor has a modification member with a height (H), and the constriction zone has a radius (R), where the physical dimension of the modification member height (H) does not exceed 0.65 times the physical dimension of the constriction zone radius (R). In other variations, the ratio of the physical dimension of the modification member height (H) to the physical dimension of the constriction zone radius (R) is in the range of about 0.16 to about 0.55. In still other variations, the enhanced eductor has a modification member with a length (L) along the main axis of the eductor, and the constriction zone has a length ($L_{CZ}$) along the main axis of the eductor, where the physical dimension of the modification member length (L) does not exceed 0.75 times the physical dimension of the constriction zone length ($L_{CZ}$). Additionally, the ratio of the modification member length (L) to the physical dimension of the constriction zone length ($L_{CZ}$) may be between about 0.25 and about 0.75. In other variations, the enhanced eductor has a modification member with a length (L) along the main axis of the eductor, and the constriction zone has a radius (R), where the ratio of the physical dimension of the modification member length (L) to the physical dimension of the constriction zone radius (R) is in the range of about 1.2 to about 3.0. Optionally, the modification member is sized such that it decreases the cross-sectional area of the constriction zone by 21% or less; and/or the spread of the protrusion of the modification member around the perimeter of the constriction zone radius (R) may be between 60 and 120 degrees. In still further variations, the presence of the modification member in the enhanced eductor element restricts the area for airflow through the hollow bore by no more than 10% when compared to an eductor element without such a modification member, but having the same inlet and outlet diameters, the same constriction zone diameter, and the same overall eductor length ($L_E$) as said enhanced eductor.

In another aspect of the invention, a breath-actuated inhalation device provided. The device features an actuation assembly including an enhanced eductor element as described above, where air flowing through the eductor element with an inspired breath acts to create a low pressure drop at the siphon channel that is suitable to actuate the device. In some variations, the breath-actuated inhalation device is a pressurized meter dose inhaler. In other variations, the breath-actuated inhalation device further includes a pressurized canister containing an aerosol formulation of drug particles, where the pressurized canister further includes a primeless valve for release of the aerosol formulation into the device upon actuation of the device.

In a still further aspect of the invention, an eductor is provided. The eductor includes an elongate conduit that has the following elements: (a) an outer surface and a bore forming an inner surface of the conduit, where the bore has a reduced diameter along a portion of the length of the elongate conduit to form a constriction zone; (b) an aperture located within the constriction zone, where the aperture forms a passage between the outer surface of the eductor and the bore; and (c) a structure that projects inwardly from the inner surface into the bore, where the structure is disposed adjacent to or around the aperture and the presence of the structure generates an enhanced negative pressure adjacent to the aperture when a flow of fluid is moving through the elongate conduit, however the presence of the structure does not generate a substantial concomitant increase in pressure resistance to the flow of fluid through the elongate conduit.

In some variations, the structure has a height (H), and the constriction zone has a radius (R), where the physical dimension of the structure height (H) does not exceed 0.65 times the physical dimension of the constriction zone radius (R). In other variations, the ratio of the physical dimension of the structure height (H) to the physical dimension of the constriction zone radius (R) is in the range of about 0.16 to about 0.55. In still other variations, the structure has a length (L) along the main axis of the conduit and the constriction zone has a length ($L_{CZ}$) along the main axis of the eductor, where the physical dimension of the structure length (L) does not exceed 0.75 times the physical dimension of the constriction zone length ($L_{CZ}$). Additionally, the ratio of the structure length (L) to the physical dimension of the constriction zone length ($L_{CZ}$) can be between about 0.25 and about 0.75. In other variations, the structure has a length (L) along the main axis of the conduit and the constriction zone has a radius (R), where the ratio of the physical dimension of the structure length (L) to the physical dimension of the constriction zone radius (R) is in the range of about 1.2 to about 3.0. Optionally, the structure is sized such that it decreases the cross-sectional area of the constriction zone by 21% or less. In still further variations, the presence of the structure in the eductor restricts airflow through the bore by no more than 10% when compared to an eductor without such a structure, but otherwise having the same physical dimensions as the eductor.

In another aspect of the invention, a breath-actuated inhalation device provided. The device features an actuation assembly including the eductor as described above, where air flowing through the eductor with an inspired breath acts to create a low pressure drop at the siphon channel that is suitable to actuate the device. In some variations, the breath-actuated inhalation device is a pressurized meter dose inhaler. In other variations, the breath-actuated inhalation device further includes a pressurized canister containing an aerosol formulation of drug particles, where the pressurized canister further includes a primeless valve for release of the aerosol formulation into the device upon actuation of the device.

It is a particular advantage of the present invention that improved performance can be obtained from eductor elements that have been modified in accordance with the invention. The enhanced eductors can be used in a breath-actuated pressurized meter dose inhaler (BApMDI) device to increase the local velocity of the flow of inspiratory breath and create a siphon suitable to actuate the device, enabling patients with compromised lung function, or adolescents without significant lung function to use these convenient and efficient drug delivery devices. It is also a particular advantage of the present invention that simple and reproducible methods of production can be used to produce the enhanced eductors of the invention.

These and other objects, aspects, variations and advantages of the present invention will readily occur to the person of ordinary skill in the art upon reading the instant disclosure and specification.

BRIEF DESCRIPTION OF THE DRAWINGS

FIG. 1 is a cross-sectional representation of a conventional eductor element.

FIG. 2 is a perspective cutaway view of the conventional eductor element of FIG. 1.

FIG. 3 is a schematic depiction of a conventional eductor element showing various important parameters thereof.

FIG. 4 is a cross-sectional representation of an enhanced eductor element produced in accordance with the invention.

FIG. 5 is a perspective cutaway view of the enhanced eductor element of FIG. 4.

FIG. 6A is a cutaway side perspective view of the modification member of the enhanced eductor embodiment of FIGS. 4 and 5, wherein the length (L) of the modification member along the long axis of the constriction zone is shown relative to the overall length of the constriction zone ($L_{cz}$) shown in FIG. 6C.

FIG. 6B is a cutaway axial view of the modification member of the enhanced eductor embodiment of FIGS. 4 and 5.

FIG. 6C is a side perspective view of the constriction zone of the enhanced eductor embodiment of FIGS. 4 and 5.

FIG. 7 depicts the performance test results (siphon pressure drop plotted against concomitant pressure drop across the eductor) for two eductor elements, a conventional eductor and an enhanced eductor element produced in accordance with the invention.

FIG. 8A presents the performance test results (a plot of the modification member height (H) against the siphon pressure drop at two different fluid flow rates) for enhanced eductors elements having Light, Medium and Heavy modification members produced in accordance with the invention.

FIG. 8B presents the performance test results (a plot of the modification member height (H) against the eductor resistance (pressure drop across the eductor) at two different fluid flow rates for enhanced eductors elements having Light, Medium and Heavy modification members produced in accordance with the invention.

Figure 9A:
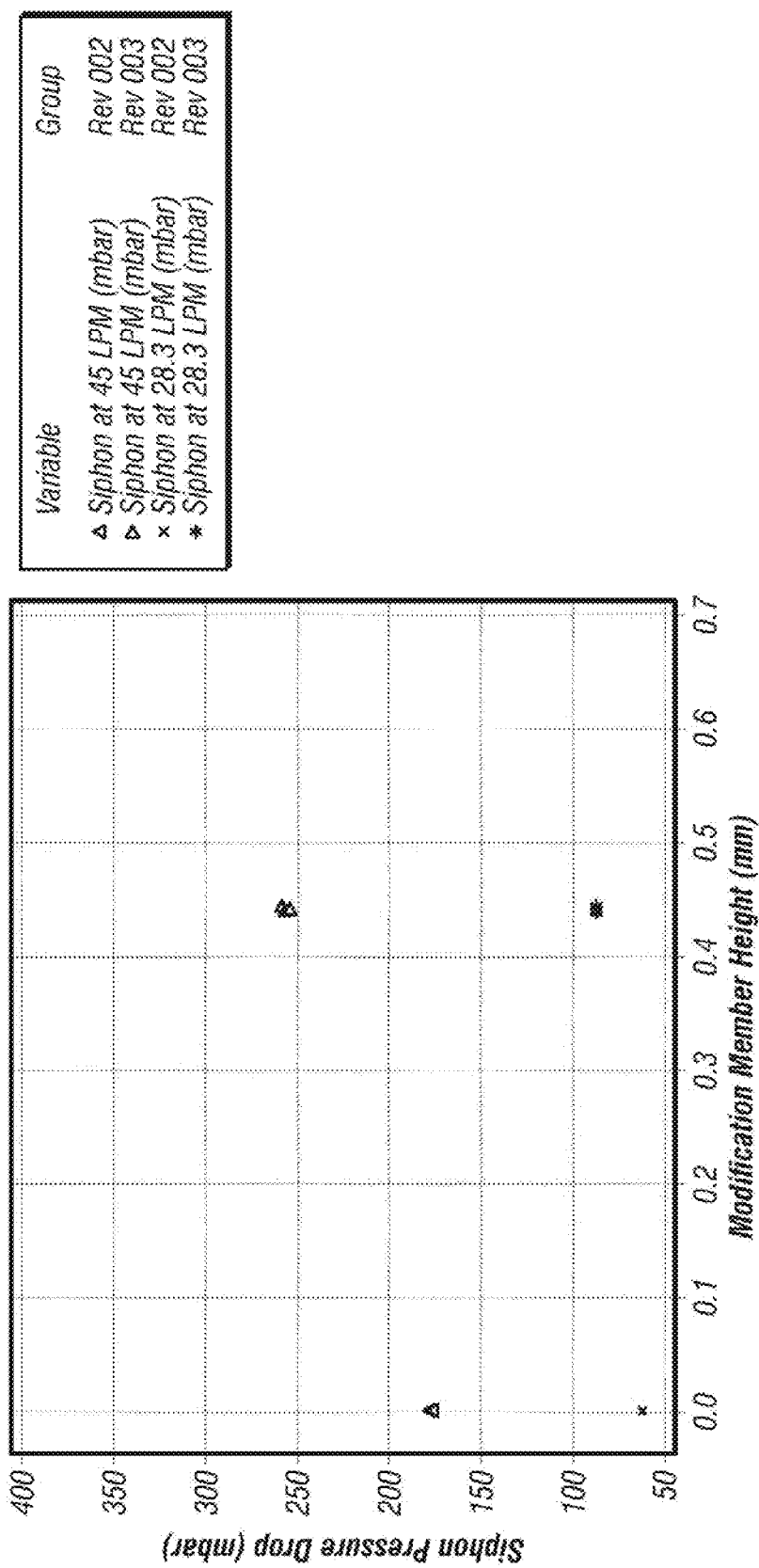

FIG. 9A compares the performance test results (a plot of the modification member height (H) against the siphon pressure drop at two different fluid flow rates) for a conventional eductor and an enhanced eductor produced in accordance with the invention.

Figure 9B:
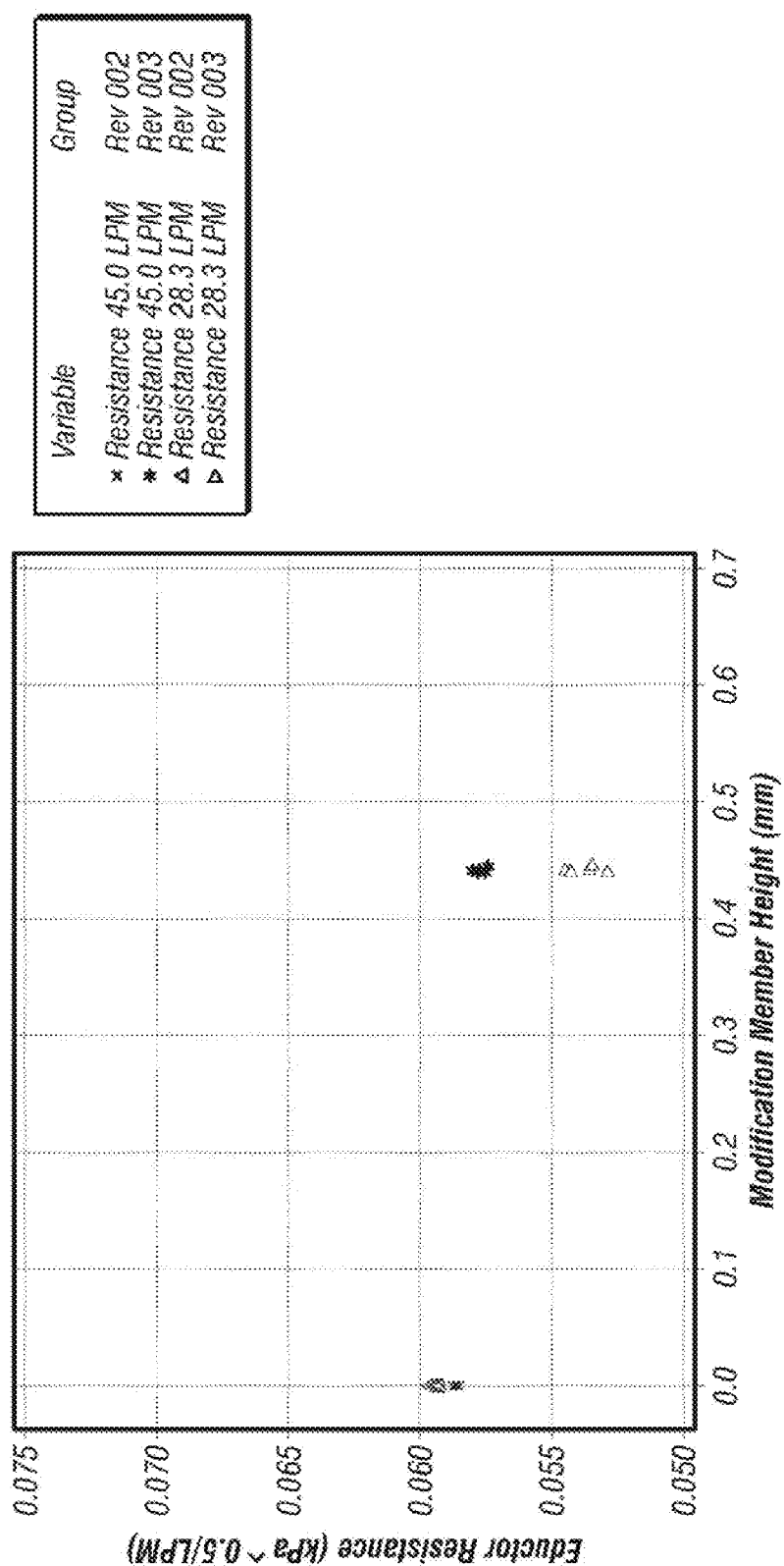

FIG. 9B compares the performance test results (a plot of the modification member height (H) against the eductor resistance (pressure drop across the eductor) at two different fluid flow rates) for a conventional eductor and an enhanced eductor produced in accordance with the invention.

Figure 10:
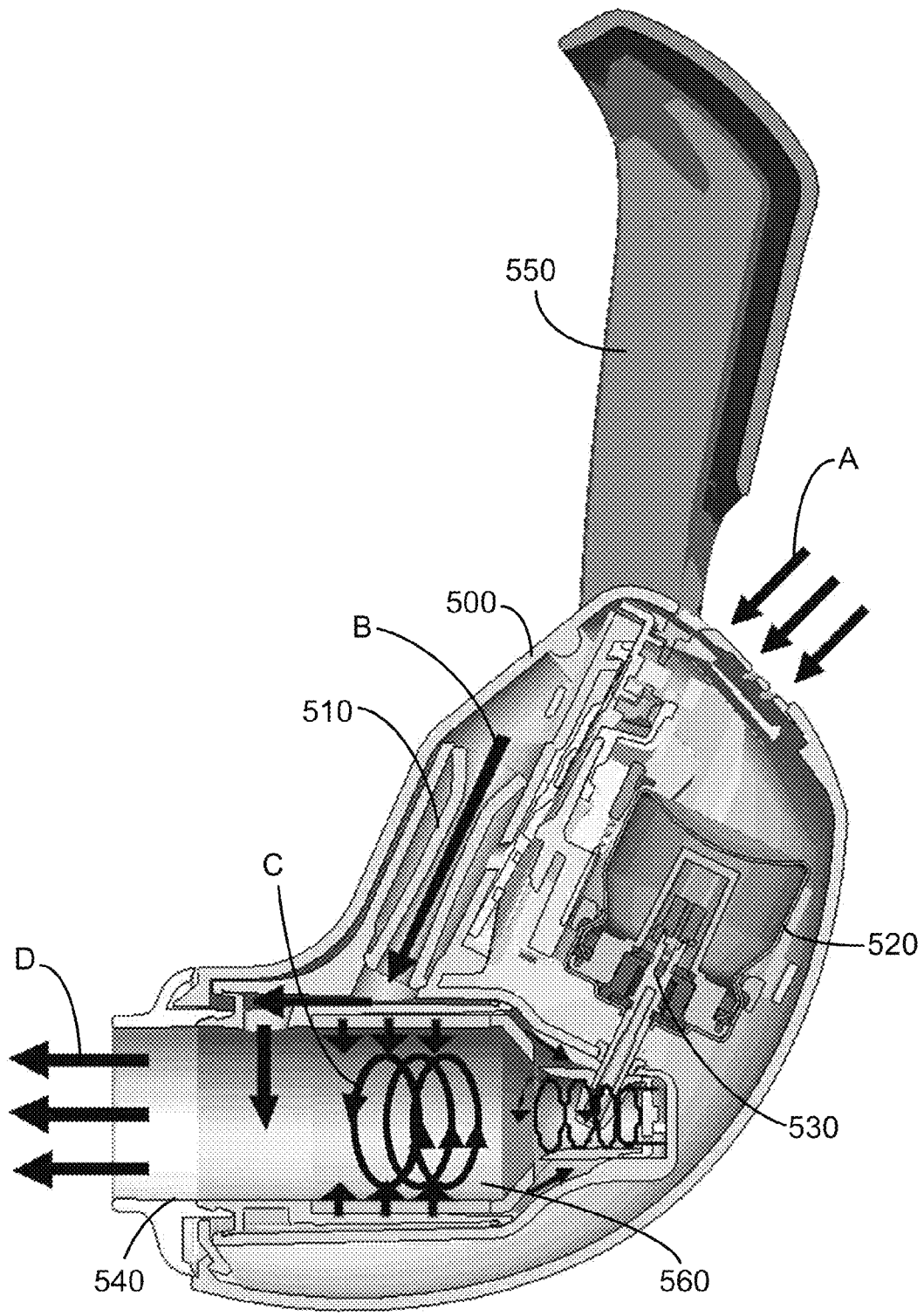

FIG. 10 depicts a cutaway view of a BApMDI device incorporating an enhanced eductor produced according to the present invention as the actuation mechanism.

DETAILED DESCRIPTION OF THE INVENTION

Before describing the present invention in detail, it is to be understood that the present invention is not limited to particularly exemplified eductor elements, breath actuated pressurized metered dose inhaler devices, or manufacturing process parameters as such may, of course, vary. It is also to be understood that the technical terminology used herein is for the purpose of describing particular embodiments of the invention only, and is not intended to be limiting.

All publications, patents and patent applications cited herein, whether supra or infra, are hereby incorporated by reference in their entirety.

As used herein, an "eductor" is an elongate conduit (hollow bore or channel) or venturi having an inlet and an outlet and through which fluid is drawn or pumped under the influence of a pressure drop applied across the inlet and outlet of the eductor. The hollow bore through the conduit usually has a cylindrical cross section, but can have ellipsoidal, oval, smoothed rectangular or other nonsymmetrical cross-section. The hollow bore has a constriction zone located within it, wherein the inlet diameter converges to a smaller diameter for a portion of the axial length to form a constriction zone, which then diverges to a diameter at the outlet that is close to that of the inlet. The convergent half angle is usually in the range of 17 to 25 degrees off the axial centerline. The divergent half angle is usually 3.5 to 7.5 degrees off the axial centerline. The axial length of the constriction zone is usually in the range of 2 to 5 diameters of the hollow bore. The ratio of the inlet diameter to the constriction diameter is referred to as choke or $1/\beta$. As fluid passes though the eductor within the constriction zone, a reduced pressure is produced as a result in increased velocity of the fluid flow through the constriction zone, the result of a Venturi Effect as described by Bernoulli's Equation. A siphon tube penetrates the conduit from the outside wall (siphon inlet) of the eductor to a location on the inside wall (siphon outlet) of the tubular duct that coincides axially with the constriction zone. Due to the Venturi Effect, named after Giovanni Venturi, a pressure drop is generated across the siphon channel that is equal to the difference in the pressure at the outside wall of the eductor, less the pressure at the inside wall of the tubular duct. The siphon pressure drop can be used to draw fluid through the siphon tube and into the tube.

Eductors are useful in many commercial applications. Eductors can be used as tank mixers. By submersing an eductor into the contents of a tank and pumping fluid through the eductor, the eductor will draw in up to 4-5 volumes of fluid for each volume pumped through the eductor. In this manner, with the use of an eductor, the same amount of mixing can be achieved with the use of a much smaller pump.

Eductors are also useful in the generation of foam for fire fighting applications. In such applications, water is pumped through an eductor that is a component for a special foaming nozzle. The water flow through the eductor draws in various foaming agents. Air is then pumped onto this mixture such that a foam is ejected from the nozzle and used to extinguish certain types of fire. Eductors are also very useful when a flammable liquid needs to be pumped and it would be dangerous to pump the flammable liquid directly with a pump.

A cross-sectional view of a conventional eductor is depicted in FIG. 1. In the figure, Arrow A shows the direction of fluid flow through Hollow Bore (110) of the Eductor (100), going from the Eductor Inlet (115) to the Eductor Outlet (120). The Siphon Inlet (115) narrows to a Constriction Zone (125). The Siphon Inlet (140) is located within the Eductor Wall (135) at a point within the Constriction Zone (125). There is a Siphon Channel (130) which penetrates the Side Wall (135) of the Eductor and penetrates through the Inner Wall (150) at Siphon Outlet (160). The surface of the Inner Wall (150) is smooth and continuous at Siphon Outlet (160) and all along the whole length of the Hollow Bore (110). This is because standard teaching provides that there should be no irregularities on the inner surface of an eductor which would cause turbulence in the fluid flow and thereby reduce the efficiency of the eductor. FIG. 2 depicts a perspective cutaway view of the Eductor (100) of FIG. 1, where Arrow A shows the direction of fluid flow through the Hollow Bore (110). Accelerated fluid flow over Siphon Outlet (160) causes a pressure drop to be drawn on the Siphon Inlet (140).

Conventional eductors such as those depicted in FIGS. 1 and 2 can be used in BApMDI devices to increase the local velocity of the flow of inspiratory breath to create a siphon suitable to actuate the device. Exemplary BApMDI devices include those devices described in U.S. Pat. Nos. 5,954,047; 6,026,808; and 6,905,141 where spring energy can be triggered by a user's breath to actuate the device. In addition, eductors are incorporated in the inhaler devices described in U.S. Pat. Nos. 5,657,749 and 6,948,496. In operation, the eductors generally consist of a venturi with a flow path diameter that narrows from the inlet to a constricted zone which increases the local velocity of the inspiratory flow. The siphon is located within the constricted zone and, per Bernoulli's Equation, the increased velocity over the Inlet Apex of the siphon generates a pressure ($P_{Inlet\ Apex}$) that is lower than the Ambient pressure ($P_{Ambient}$) entering the eductor, thus creating a siphon. In BApMDI devices, the siphon is connected to a variable volume chamber. As the siphon draws air into the constricted region of the eductor the variable volume chamber is evacuated. At a triggering point, the variable volume chamber has been evacuated sufficiently to collapse, thus tripping the discharging mechanism of the BApMDI (e.g., release of a compressed spring). By appropriate selection of design parameters, such as the chamber volume, the eductor size, shape and configuration, and the siphon diameter, the BApMDI device can be designed to cause actuation with a desired amount of force of the inspiratory breath. This mechanism enables consistent discharge timing that is appropriate for lung delivery and automatically adjusts to the inspiratory pattern for a wide range of users.

It is generally understood in the art that, by applying Bernoulli's equation, the siphon pressure drop generated by an eductor can be increased by narrowing the diameter of the constricted zone, that is, by increasing the choke of the eductor. This can be a very useful parameter to adjust the triggering mechanism in BApMDI devices for configurations where considerable force is required to actuate the device in a timely manner. However, as the constriction zone diameter narrows, it becomes harder to move air through the eductor and the pressure drop across the eductor increases according to Pousieulles' Equation. As a result, modification of an eductor to increase constriction (choke) might render a BApMDI device inoperative as some users may not have sufficient pulmonary function to trigger a device with such increased constriction and increased eductor pressure drop. Accordingly, there is a significant engineering trade-off in terms of designing an improved eductor for use in a BApMDI device. Specifically, any increases in the constriction (increased choke) of the eductor would be expected to cause a concomitant increase in the pressure drop drawn on the siphon tube (the siphon pressure drop), and thereby increase actuation force. However, any such decrease in the diameter of the constriction zone would cause a greater resistance to fluid flow through the eductor, resulting in a pressure drop across the eductor, possibly frustrating any increases realized with the enhanced siphon pressure drop. This can be thought of as trying to draw fluid from a cup through a series of smaller and smaller straws. Accordingly, application of the engineering technique of significantly increasing choke to increase the siphon pressure drop (and thus increase actuation force) would be expected to render the eductor inoperative, since a user trying to inspire through the constricted eductor would find it difficult or impossible to draw a normal breath across such an eductor having such a significant constriction.

It has been serendipitously discovered that introducing a protrusion or structure (effectively, a structural constriction) occupying a highly localized area within the constriction zone adjacent to the apex of the siphon inlet can dramatically increase the siphon pressure drop in an eductor without significantly increasing the pressure drop across the eductor. These localized structures or protrusions are referred to herein as a "modification member". Use of the enhanced eductor design in a BApMDI device to actuate the device means that even compromised users can now actuate such devices even if they require an increased siphon pressure drop to operate the device correctly. The modification member (highly localized protrusion or structure) was unintentionally discovered when the inventors inserted a sharp probe into the siphon aperture of a conventional eductor from outside of the eductor as part of the process of inserting that eductor into a bench testing apparatus. Insertion of the probe into the plastic eductor aperture caused deformation of the plastic around the inside perimeter of the aperture and the creation of a small conical frustum-shaped protrusion in the constriction zone bore of the eductor. Upon subsequent testing of the eductor performance with the bench testing apparatus, the eductor siphon pressure was found to dramatically increase, however there was no significant (deleterious) pressure drop across the eductor. Subsequent testing confirmed the phenomena, and specific modifications have now been designed into the enhanced eductor designs (and injection molding equipment fabricated) to create effective modification members in the constriction zone of the eductor.

Referring now to FIG. 3, in order to describe the present invention, several important features of an eductor are depicted. Three primary parameters of the eductor include the length of the eductor ($L_E$), the inside diameter of the inlet ($D_i$) and the inside diameter of the outlet ($D_o$). Another important parameter is the diameter of the throat ($D_t$). The eductor narrows from $D_i$ to $D_t$ through what is called the convergent zone. There is then a region having the diameter of the throat ($D_t$) which is called the constriction zone. Then the diameter increases again until outlet diameter ($D_o$) is reached which is usually equal to the inlet diameter ($D_i$). This region is called the divergent region. Siphon pressure drop, and pressure drop across the eductor can be determined using the following measurements: the pressure at the inlet ($P_{Inlet}$) of the eductor; the pressure at the outlet ($P_{Outlet}$) of the eductor; the ambient pressure entering the eductor at the siphon ($P_{Ambient}$); and the pressure at the apex of the inlet ($P_{Inlet\ Apex}$).

With reference to "*Fluid Meters, Their Theory and Application, Report of ASME Research Committee on Fluid Meters*", 6th Edition (1971), the siphon pressure drop ($\Delta P_{siphon}$) generated by the eductor siphon is described by Bernolli's Equation for invisid subMach 1 flow:

$$\Delta P_{siphon}=(P_{Ambient}-P_{Inlet\ Apex})=Q^2\rho(1/A^2-1/a^2)2g_c(g_f/cm^2)\text{, where:}$$

$\rho$=standard temperature and pressure (STP) air density throughout=0.001193 gm/cm$^3$;

$g_c$=gravitational constant=982.14 ($g_m/g_f$) (cm/sec$^2$);

a=throat cross sectional area=$\pi D_t^2/4$; and

A=Inlet cross sectional area=$\pi D_i^2/4$.

The flow and pressure drop through any conduit with laminar flow can be described by Poiseulle's Equation:

$$Q=\text{volumetric flowrate}=g_c\rho(P_{Inlet}-P_{Outlet})d^4/128mL_E\ (cm^3/sec).$$

Thus, the pressure drop across the eductor ($\Delta P_{eductor}$) can then be determined by rearranging Pouiseulle's Equation and including a loss factor ($1-\Delta P_{Eloss}$) which is a function of the venturi $\alpha_2$ and $\beta$:

$$\Delta P_{eductor}=(P_{Inlet}-P_{Outlet})=Q128\ \mu L_E/\pi g_c D_{mean}^4(1\Delta P_{Eloss})(g_f/cm^2)\text{, where:}$$

$\alpha_2$=divergent nozzle ½ angle=7.5 degrees;

$\beta$=throat diameter divided by the inlet diameter ($D_t/D_i$)=0.339 $g_m$/sec-cm;

air viscosity at STP $\mu_{air}$=0.000179; and $\Delta P_{Eloss}$=diff. Pressure Loss (%)=$e^{(1.883+(0.253\alpha 2)+(-0.327\beta\alpha 2)+(0.494\beta))}$ Using the above-described mathematical techniques, both the siphon pressure drop and the pressure drop across the entire eductor can be predicted at various flow rates for proposed eductor designs of known dimensions. These predicted pressure drops can then be compared to measured pressure drop values of various model eductors. Surprisingly, when the above-described techniques are applied to the enhanced eductor designs of the present invention, the predicted values fail to adequately describe the measured eductor performance. In particular, when there is a predicted increase in siphon pressure drop (based upon the added constriction provided by the modification member in the constriction zone), the corresponding predicted values for pressure drop across the eductor significantly over-estimate the magnitude of that pressure drop. In fact, significant increases in siphon pressure drop can be achieved with the enhanced eductor designs of the present invention without a concomitant unwanted increase in pressure drop across the eductor. In some cases, the enhanced eductor designs of the present invention significantly increase siphon pressure drop with a minimal reduction in pressure drop across the eductor of 10% or less. This results in eductor designs that have dramatically improved performance characteristics.

The enhanced eductors of the present invention comprise a modification member (protrusion or structure) that is located on the inner wall of the eductor in the constriction zone. The size and shape of the protrusion or protrusion is restricted to a volume surrounding the siphon outlet, defined by a length (L) along the long axis of the constriction zone, a height (H) which is the maximum amount that the protrusion or structure projects above the surface of the constriction zone, and a segment of the curvilinear surface (θ or Theta) formed by the constriction zone wall (a cross-sectional arc having an angle relative to the minor axis of the constriction zone). In certain embodiments, the siphon channel extends through the modification member, and preferably the siphon channel extends through the axial middle of the protrusion or structure that forms the modification member. In other embodiments, the protrusion or structure is adjacent to the siphon outlet. The protrusion or structure causes an increased reduction in pressure just in the location surrounding the siphon inlet apex, which increases the local velocity of the fluid flow and results in a reduction of pressure at the apex. There is however little or no increase in flow resistance because of the decrease in the cross-sectional area of the eductor conduit if the following key parameters of the protrusion or structure are met: the height (H) of the protrusion or structure does not exceed 0.65 times the radius (R) of the constriction zone; the length of the protrusion or structure along the eductor long axis (L) does not exceed 0.75 times the length of the constriction zone ($L_{CZ}$); and the spread of the protrusion or structure around the perimeter of the constriction zone radius (θ) does not exceed 120 degrees, such that the protrusion or structure that forms the modification member decreases the constriction zone cross-sectional area by about 21% or less. In certain embodiments, the ratio between the height (H) of the protrusion or structure and the radius (R) of the constriction zone is between about 0.16 and 0.55. In further embodiments, the ratio between the length of the protrusion or structure along the eductor long axis (L) and the radius (R) of the constriction zone is between about 1.2 and 3.0. In still further embodiments, the spread of the protrusion or structure around the perimeter of the constriction zone radius (θ) is between about 30 and 80 degrees.

Figure 4:
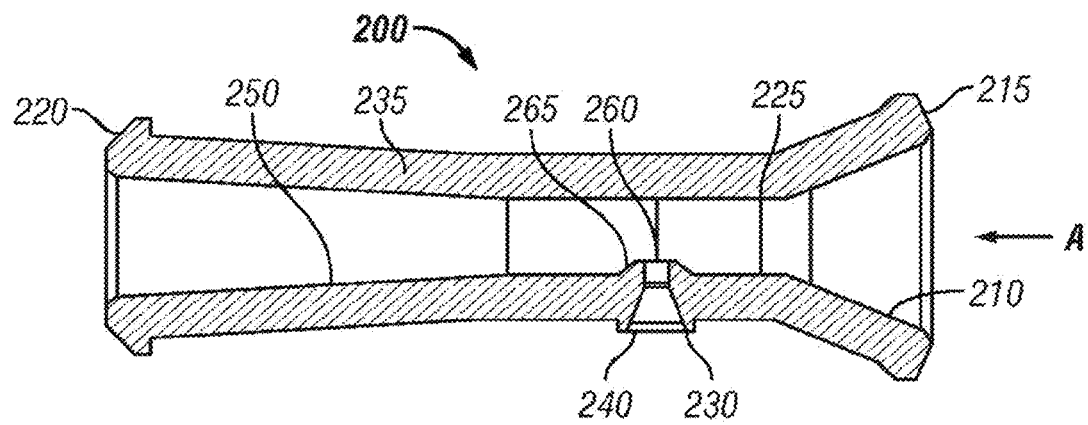
Figure 5:
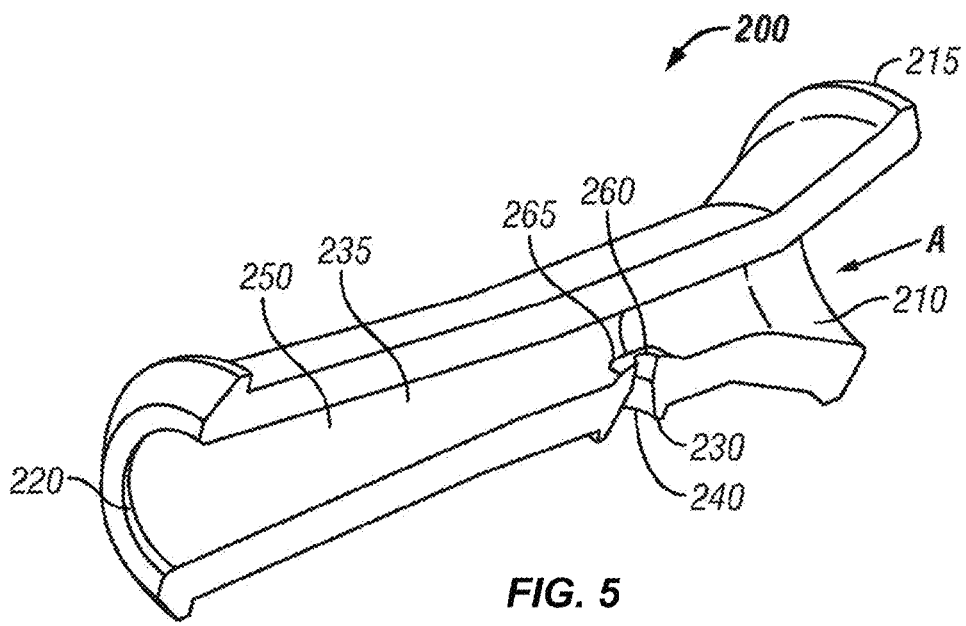

A cross-sectional view of an embodiment of an enhanced eductor of the present invention is depicted in FIG. 4. In the figure, Arrow A shows the direction of fluid flow through Hollow Bore (210) of the Eductor (200) going from the Eductor Inlet (215) to the Eductor Outlet (220). The Siphon Inlet (215) narrows to a Constriction Zone (225). The Siphon Inlet (240) is located within the Eductor Wall (235) at a point within the Constriction Zone (225). There is a Siphon Channel (230) which penetrates Side Wall (235), and passes through the Inner Wall (250). The Siphon Channel (230) also passes through the protrusion or structure provided by the Modification Member (265), and terminates at the Siphon Outlet (260). FIG. 5 depicts a perspective cutaway view of the Eductor (200) of FIG. 4, where Arrow A shows the direction of fluid flow through the Hollow Bore (210). Accelerated fluid flow over the Modification Member (265) and Siphon Outlet (260) causes an enhanced siphon pressure drop to be drawn on the Siphon Inlet (240) without a concomitant inappropriate increase in the pressure drop across the eductor. Accordingly, there is little to no significant increase in flow resistance through the eductor despite the decrease in the cross-sectional area of the constriction zone in the eductor bore.

FIG. 6A is a cutaway side perspective view of the Modification Member (265) of eductor embodiment of FIGS. 4 and 5, wherein the length (L) of the Modification Member along the long axis of the constriction zone is shown relative to the overall length of the constriction zone ($L_{CZ}$) in the embodiment of FIGS. 4 and 5. FIG. 6B is a cutaway axial view of the Modification Member (265) of the eductor embodiment of FIGS. 4 and 5, wherein the height (H) of the Modification Member (265), and the segment of the curvilinear surface (θ) formed by the constriction zone wall of the modification member is also shown.

Figure 7:
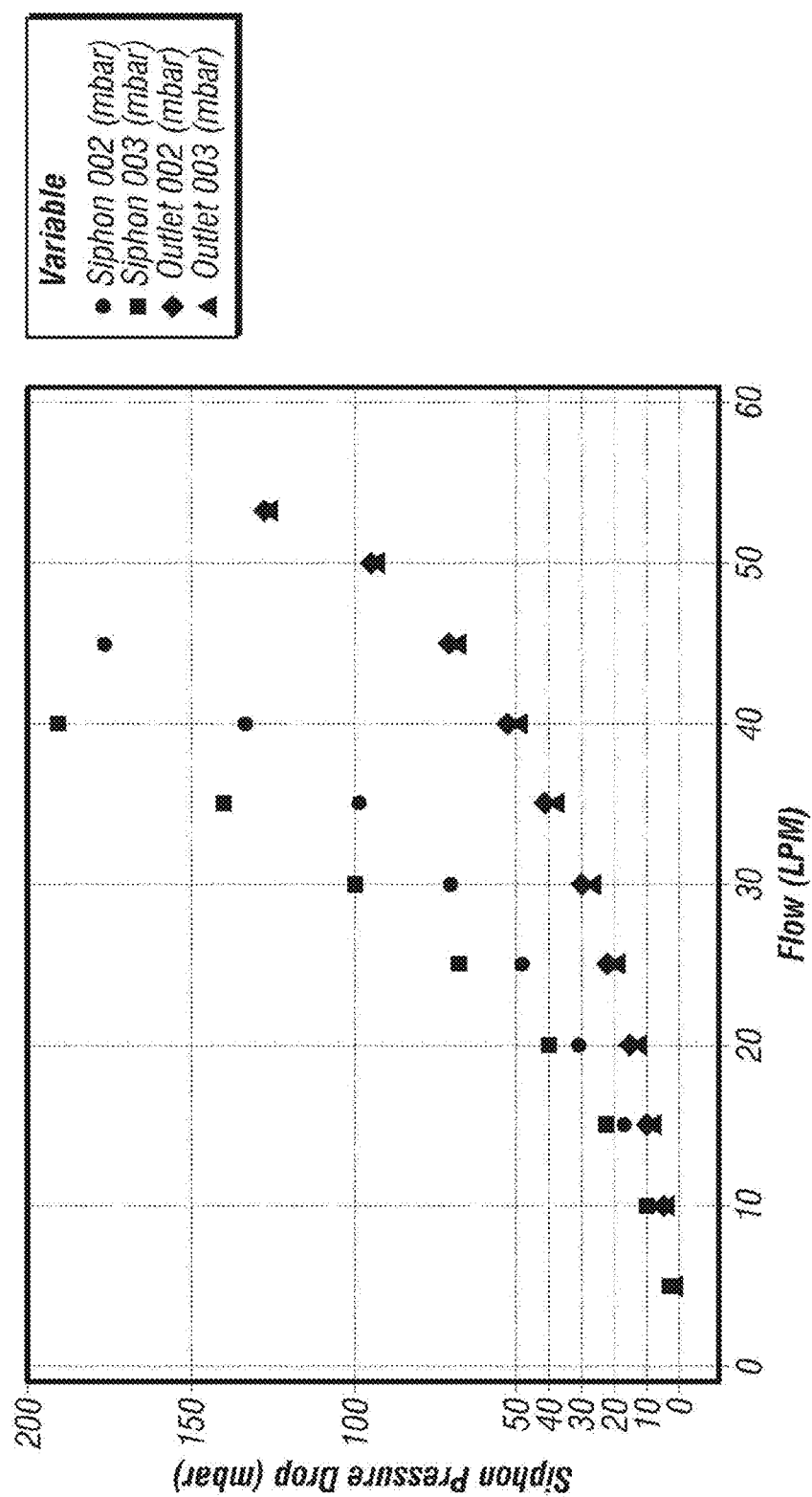

In order to demonstrate the improved performance of an enhanced eductor element according to the present invention, two eductors having identical primary eductor parameters (identical eductor lengths ($L_E$), identical inlet inside diameters ($D_i$), identical outlet inside diameters ($D_o$), identical throat diameters ($D_t$), and identical constriction zone lengths ($L_{CZ}$)) were produced. The first eductor (002) was a conventional eductor, and the second eductor (003) included a modification member in the constriction zone produced in accordance with the present invention. The two eductor elements were tested for siphon pressure drop and for pressure drop across the eductor. FIG. 7 depicts the results of the testing of the eductors at various flow rates, in particular, showing a plot of the flow through the eductor horizontal axes as plotted against the siphon pressure drop (vertical axis) generated for the conventional eductor (002) and the enhanced eductor (003) that was modified according to the present invention. There are 4 data points located at each horizontal data point. The diamond (♦) represents the resistance (pressure drop across the eductor) through the conventional eductor (002), and the triangle (▲) represents the resistance (pressure drop across the eductor) through the enhanced eductor (003). As can be seen, at the various test flow rates (5, 10, 15, 20, 25, 30, 35, 40, 45, and 55 liters per minute (LPM)), the two data points (♦ and ▲) representing the pressure drop across the eductors for the two different educators are almost identical, demonstrating that the addition of the modification member in the enhanced eductor (003) did not result in the increase in flow resistance through that eductor despite the decrease in the cross-sectional area of the constriction zone in the eductor bore.

However, when the siphon pressure drop for the two eductors was measured, there was a significant difference seen between the convention eductor (002) and the enhanced eductor (003). Referring again to FIG. 7, the siphon pressure drop generated at the siphon outlet for the conventional eductor (002) is represented by the circle (●), and the siphon pressure drop generated at the siphon outlet for the enhanced eductor (003) is represented by the square (■). As can be seen, as the flow rate value increases (going from left to right along the horizontal axis) the difference between the siphon pressure drop for the convention eductor (002) and the enhanced educator (003) increases significantly. For example, at 40 LPM (generally the velocity of a normal inspiratory breath), the enhanced eductor siphon pressure drop (■) is almost 60 mbar higher than that for the conventional eductor pressure drop (●), which is surprising since the concomitant pressure drop across both eductors varied from one another by only about 2-3 mbar. In fact, at most of the flow rates associated with a normal inspiratory breath (25 to 40 LPM), the enhanced eductor (003) had significantly increased siphon pressure drop and a concomitant lower resistance (pressure drop across the eductor) when compared to the conventional eductor (002). This was an unexpected result in light of typical eductor design principals which teach that any increase in the obstruction of a flow path (presence of the modification member) should result in a higher resistance.

In order to further demonstrate the improved performance of enhanced eductor elements produced according to the present invention, a number of eductors having identical primary eductor parameters (identical eductor lengths ($L_E$), identical inlet inside diameters ($D_i$), identical outlet inside diameters ($D_o$), identical throat diameters ($D_t$), and identical constriction zone lengths ($L_{CZ}$)) were produced. The first eductor (Rev 002) was a conventional eductor produced by injection molding. The second eductor (Rev 003) was also produced by injection molding and included a molded modification member (with a protrusion height (H) of 0.45 mm) in the constriction zone and encircling the siphon outlet to form an enhanced eductor element in accordance with the present invention. Next, conventional eductors produced by the same injection molding process used to produce the (Rev 002) eductor were hand-altered to produce three groups of modification members in accordance with the present invention. In particular, three groups of enhanced eductors, referred to herein as Heavy, Medium and Light, respectively, were formed manually by the introduction of a tapered tool into the siphon channel. Insertion of the tapered tool into the siphon channel caused deformation of the molded plastic of the eductor, resulting in "volcano-shaped" modification members within the hollow bore of the eductor and encircling the siphon outlet. The amount of force used to insert the tapered tool was subjectively applied as Light, Medium and Heavy to produce modification members having a range of different protrusion heights (H). The actual protrusion height (H) for each eductor element in the Light, Medium and Heavy modification member groups was then measured optically. The diameter of the hollow bore in the constriction zone of all of the eductor elements was 2.54 mm, and thus the radius (R) of the constriction zone was 1.27 mm. The optically measured heights (H) of the modification members in the Light, Medium and Heavy enhanced eductor groups ranged from about 0.2 mm to about 0.7 mm.

Figure 8A:
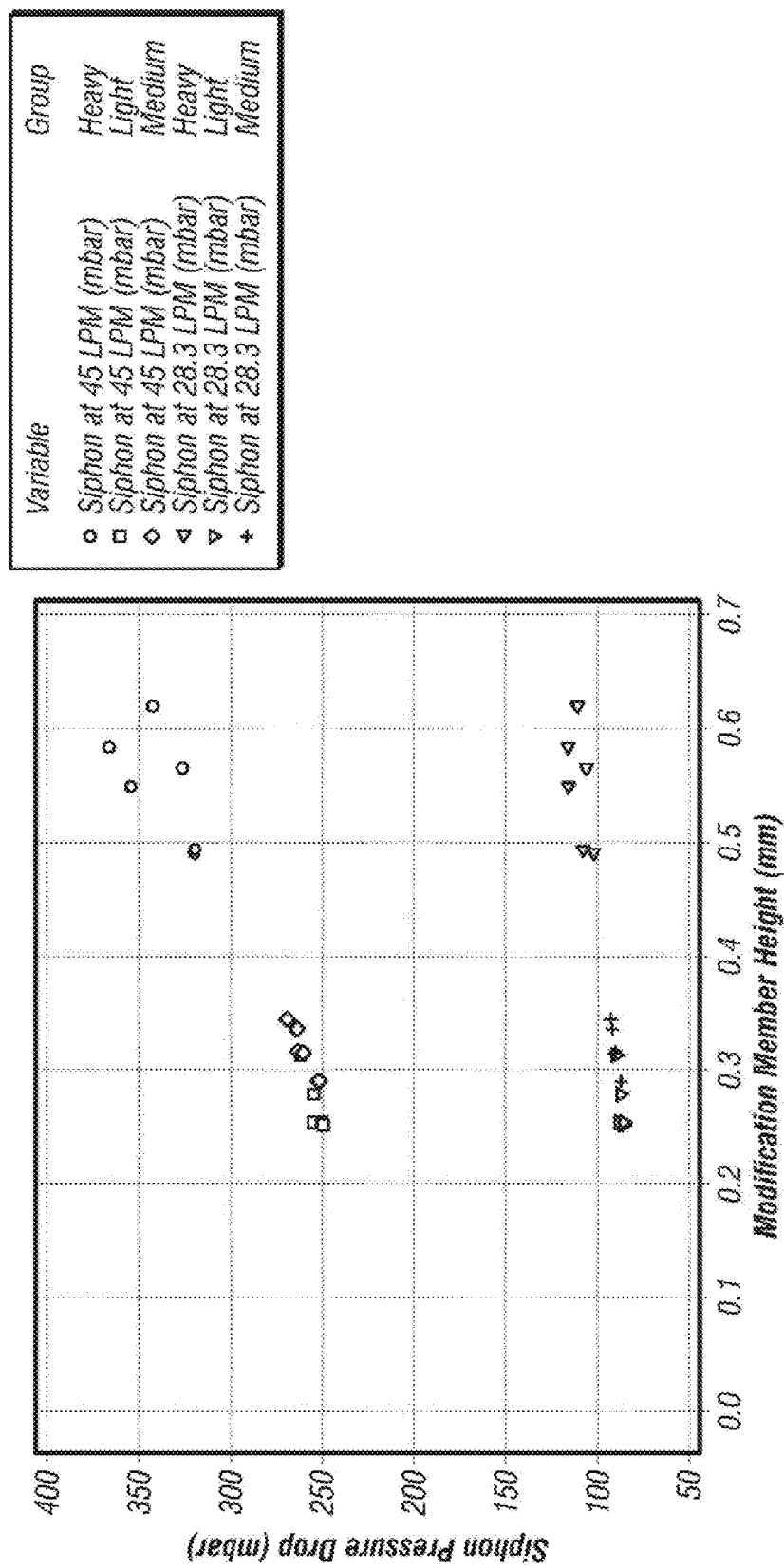
Figure 8B:
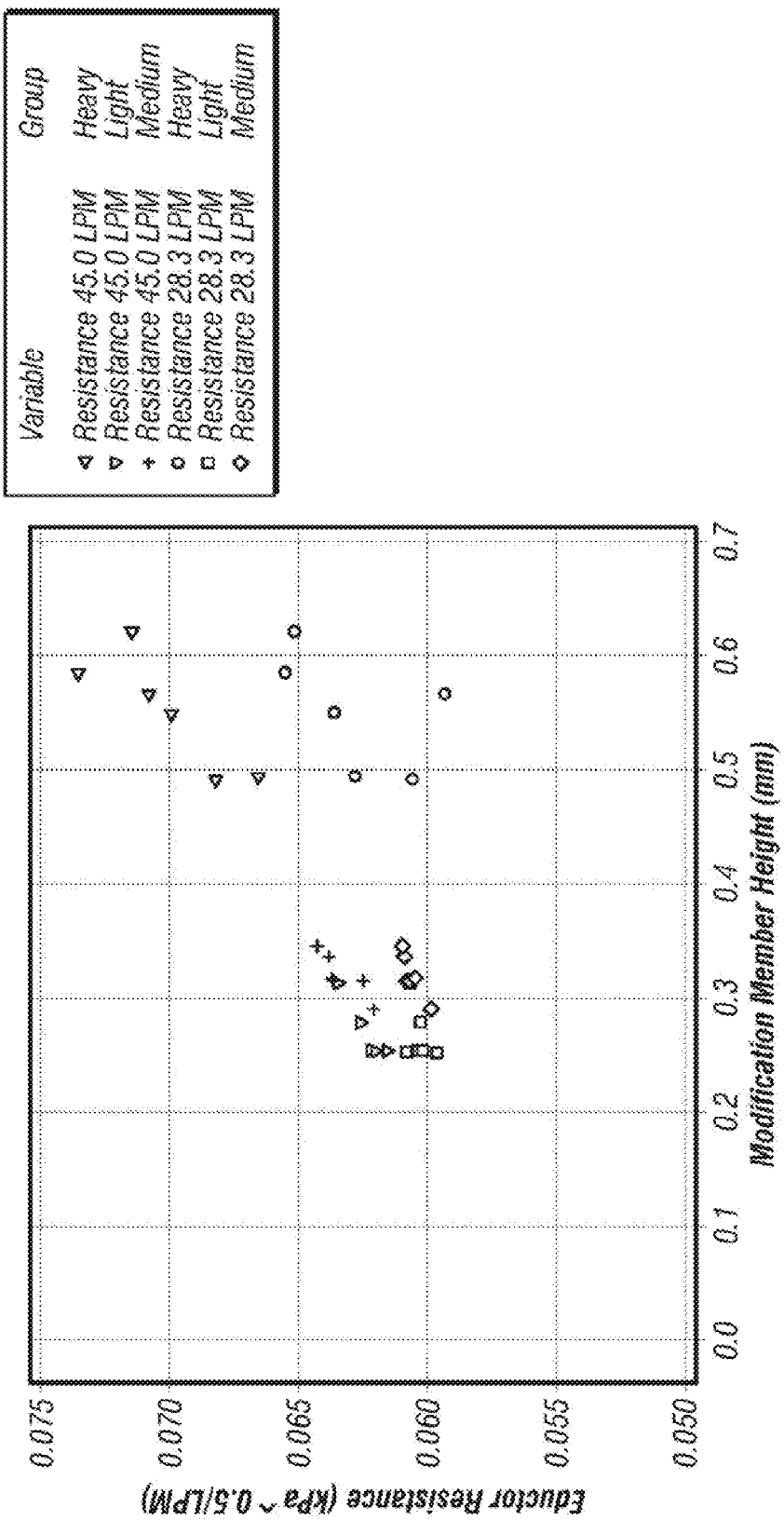

Referring now to FIG. 8A, a plot of the modification member heights (H) vs the siphon pressure drop at two flow rates (28.3 LPM and 45 LPM) for the Light, Medium and Heavy modification member groups is presented. As can be seen, all of the hand-modified enhanced eductors showed increased eductor efficiency, where the siphon pressure drop at the lower fluid flow rate (28.3 LPM) ranged from about 80 mbar (for the Light modification member group) to about 120 mbar (for the Heavy modification member group). The siphon pressure drop at the higher fluid flow rate (45 LPM) ranged from about 250 mbar (for the Light modification member group) to about 375 mbar (for the Heavy modification member group). The concomitant eductor resistance (pressure drop across the eductor) for the Light, Medium and Heavy modification member groups is presented in FIG. 8B. In particular, a plot of the modification member heights (H) against the eductor resistance (pressure drop across the eductor) at two flow rates (28.3 LPM and 45 LPM) for the Light, Medium and Heavy modification member groups is presented in FIG. 8B. As can be seen, the eductor resistance at the lower flow rate (28.3 LPM) ranges from about 0.060 $KPa^{0.5}/LPM$ (for the Light modification member group) to about 0.063 $KPa^{0.5}/LPM$ (for the Heavy modification member group). The eductor resistance at the higher fluid flow rate (45 LPM) ranged from about 0.063 $KPa^{0.5}/LPM$ (for the Light modification member group) to about 0.070 $KPa^{0.5}/LPM$ (for the Heavy modification member group). Accordingly, even though the Light, Medium and Heavy modification member groups showed significantly enhanced siphon pressure drop performance that increased in a substantially linear fashion with increases in the height (H) of the modification members, the concomitant eductor resistance performance remained relatively unchanged across all three groups.

In comparison to the eductor performance results obtained with the hand-modified enhanced eductors (the Light, Medium and Heavy modification member groups), the performance of the conventional eductor (Rev 002) and the injection molded enhanced eductor (Rev 003) were tested using the same test parameters. Referring now to FIG. 9A, a plot of the modification member heights (H) against the siphon pressure drop at two flow rates (28.3 LPM and 45 LPM) for the conventional eductor (Rev 002), where (H)=0, and the injection molded enhanced eductor (Rev 003), where (H)=0.45 mm, is presented. As can be seen, the enhanced eductor (Rev 003) showed increased eductor efficiency as compared with the conventional eductor (Rev 002), where the siphon pressure drop at the lower fluid flow rate (28.3 LPM) was about 60 mbar (for the Rev 002 conventional eductor) as compared with about 250 mbar (for the Rev 003 enhanced eductor); and the siphon pressure drop at the higher fluid flow rate (45 LPM) was about 175 mbar (for the Rev 002 conventional eductor) as compared to about 255 mbar (for the Rev 003 enhanced eductor). The concomitant eductor resistance results (pressure drop across the eductor) for the conventional eductor (Rev 002) and the injection molded enhanced eductor (Rev 003) are presented in FIG. 9B. In particular, a plot of the modification member heights (H) against the eductor resistance (pressure drop across the eductor) at two flow rates (28.3 LPM and 45 LPM) for the conventional eductor (Rev 002) and the injection-molded enhanced eductor (Rev 003) is presented in FIG. 9B. As can be seen, the eductor resistance at the lower flow rate (28.3 LPM) was about 0.059-0.060 $KPa^{0.5}/LPM$ for the Rev 002 conventional eductor (as compared to about 0.053-0.055 $KPa^{0.5}/LPM$ for the Rev 003 enhanced eductor). The eductor resistance at the higher fluid flow rate (45 LPM) was about 0.059 $KPa^{0.5}/LPM$ for the Rev 002 conventional eductor (as compared to about 0.057 $KPa^{0.5}/LPM$ for the Rev 003 enhanced eductor). Accordingly, the enhanced eductor (Rev 003) demonstrated comparable performance enhancements with the Light, Medium and Heavy modification member enhanced eductors (increased siphon drop without a concomitant increase in resistance pressure), and was demonstrably superior to the convention eductor (Rev 002) in both siphon pressure drop and resistance pressure performance.

Yet a further example of the benefits provided by the enhanced eductor designs of the present invention is that the enhanced eductors display a greatly improved triggering consistency, a key quality performance attribute for BApMDIs. In this regard, BApMDI devices containing eductor elements must be quality tested to demonstrate acceptability for use in a human pharmaceutical product. Accordingly, devices that have been manufactured for use in human pharmaceutical products are tested for actuation pressure performance and consistency to ensure acceptable pharmaceutical performance. The testing parameters set an acceptable upper and lower limit of device (breath) actuation pressure at 47 and 25 mbar, respectively. The lower limit is set at a high enough pressure to avoid accidental triggering of the inhaler, and the upper limit is set at an empirically set value which reflects an upper value for inspiratory breath pressure which a normal person would find comfortable. In quality testing of the required actuation pressure for a sampling of BApMDI devices containing a conventional eductor, a significant number of units tested were found to be well above the upper actuation pressure limit, and 70% of the tested devices therefore failed to meet the quality specification. However, when a similar sampling of BApMDI devices containing an enhanced eductor element produced in accordance with the present invention were quality tested, only 15% of the tested devices failed to meet the quality specification. This represents a significant improvement in manufacturing efficiency as a result of switching from the use of a conventional eductor to the eductors of the present invention, which can be reflected in significant improvement in the overall cost of goods for such pharmaceutical products.

The enhanced eductors of the present invention may be manufactured using standard processes and techniques known to the person of ordinary skill in the art and using materials that are readily available. Accordingly, enhanced eductors can be formed from plastic materials, e.g., pharmaceutical grade plastics such as polycarbonates (Makrolon, part number 2458-550115, Bayer MaterialScience), using a standard injection molding process. In one preferred embodiment, the enhanced eductors are formed from a polycarbonate material using an injection molding technique employing three pins (one pin extending from the eductor inlet to the middle of the modification member over the middle of the siphon outlet; a second pin extending from the eductor outlet to the middle of the modification member over the middle of the siphon outlet and meeting the first pin; and a third pin extending from the siphon inlet to the siphon outlet and meeting the first and second pins). The mold components including the pins are preferably finely polished to avoid generation of any surface irregularities on the inside surface and along the entire length of the eductor bore including the surfaces of the modification member.

Once manufactured, there are numerous applications where the enhanced eductors of the present invention may be advantageously applied. One such application is in the triggering mechanism of a breath-actuated inhaler, where a human inhalation provides the triggering energy for actuation of the device. In this regard, it is often the case that the energy (pressure drop) required to trigger a breath-actuated inhaler is greater than that which can be applied by a normal human breath. This instant invention provides a means to amplify the pressure drop across the siphon, which if advantageously coupled to a triggering mechanism enables actuation with a normal human breath. The ability to increase the pressure drop across the siphon of the enhanced eductor without a proportionate increase in the eductor pressure drop enables even human subjects such as small children and those compromised by health conditions to operate a breath-actuated triggering mechanism.

Delivery of drugs, either local or systemically, via delivery of powders, mists and aerosols to the lungs has been in use for decades. Nebulizers typically generate mists or aerosols which are delivered into the air stream being inhaled by the patient. The aerosols and mists are often generated by forcing compressed air through a solution of the medication or by the use of vibrating meshes which force the solution of the medication through apertures in the mesh to generate very small droplets of the medication solution. The generated aerosol is delivered to the patient by way of tubing and/or a face mask which is held in place over the nose and mouth of the patient who breathes in normally. The advantage of this feature is that the patient is only required to breathe in through the face mask in a normal fashion. There is no need to synchronize the breathing with the nebulizer, because the nebulizer continuously delivers the medicated mist to the patient which makes a nebulizer particularly useful for treating pediatric patients.

For non-pediatric patients, metered dose inhalers (MDIs, also referred to as pressurized MDIs or pMDIs) were developed, which are hand-held and do not require ancillary equipment or electricity. MDI devices typically consist of a small aluminum canister containing pressurized gas and a medication formulation, which is either a solution and/or a suspension of the medication. The canisters have a metering valve which will deliver a single small bolus (typically 25-100 mL) of the formulation when the stem of the valve is compressed. The MDI inhaler device can be made up of a simple plastic housing into which the canister is inserted with the valve end of the canister placed into the housing. A portion of the bottom of the canister is exposed above the housing so that it can be manually pushed further down into the housing. This action causes the valve stem to be pushed into the body of the valve and releases a bolus of the medication into the housing.

In use, a patient holds the mouthpiece of the MDI device up to his/her mouth, starts to take a breath and then manually releases a bolus of the medication by pushing down on the canister. This releases an aerosol bolus of the medication into the air stream created by the inhalation of the patient. This combination of manual dexterity and breath timing effectively excludes small children from using MDI devices effectively, but a number of adults also find it difficult to use such MDI devices properly. In order to address these concerns, breath-actuated MDI devices were developed. Early versions included advanced housings into which a standard manual MDI device is placed. There are both mechanical and electronic versions which detect the air flow caused by the patient inhaling and then cause the canister to be automatically depressed in order to deliver the medication.

There are a number of breath-actuated inhaler devices in which the pressurized canister is activated in various ways by the flow of inspiratory breath of the patient. Many are activated by placing a pivotable plate that is positioned in the air flow and mechanically linked so that rotation of the plate triggers the release of some type of stored energy to activate a metered dose inhaler (MDI) canister valve. U.S. Pat. Nos. 5,954,047; 6,026,808; and 6,905,141 describe a breath-actuated pressurized MDI (BApMDI) device in which a spring is compressed by opening a cover and then the stored energy of the spring is released by the patient breathing in though the mouthpiece. The flow of inspiratory air moves through a conventional eductor which causes the volume of a variable volume chamber to be reduced by the vacuum drawn on the vacuum chamber through the siphon tube. As the vacuum chamber size decreases, this mechanically causes a trigger to be released and the stored spring energy to bias the medicament canister downwards which activates the metering valve and dispenses a dose of the medicament. There are various such BApMDI devices currently being manufactured, such as the TEMPO® BApMDI device (MAP Pharmaceuticals), and the Maxair® Autohaler®, and EasiBreathe MDI devices (Teva). Because the enhanced eductors of the present invention can, in effect, be used to amplify the force of any fluid flow, such elements can be used in any type of device or apparatus where such pressure amplification would be of benefit.

In certain embodiments of the invention, the enhanced eductor is used to provide an improved version of a TEMPO BApMDI device (MAP Pharmaceuticals, Inc.). This device includes the breath-actuated MDI inhaler device (actuator) containing a pressurized canister, having a primeless valve assembly and containing an aerosol formulation with a suspension of powdered medicament. The valve assembly contains a thermoplastic core, body, and metering chamber and a spring. The valve assembly has been specifically designed to allow the pressurized contents of the canister to freely flow into and out of the metering chamber. The free flow of the formulation into and out of the metering chamber is achieved by the specific design of the flow path between the canister and the metering chamber. As the valve primes when it is inverted for use, there is no need to fire any wasted priming shots. The valve is intended to be used in the inverted (valve down) orientation, with a suitable delivery actuator.

The valve is actuated by depressing the core into the valve (by pushing onto the canister base on inverted valve when used with an actuator). The valve is designed such that on depressing the core and prior to the side hole of the core entering the metering chamber, the slot at the lower end of the core within the chamber passes beyond the inner seat, closing the chamber to the formulation. Further depression of the core allows the side hole of the core to enter the metering chamber, permitting it to discharge the formulation through the hollow stem. When the core is returned by the spring to its rest position, the slot at the lower end of the core enters the metering chamber allowing the chamber to be refilled. The valve is thus primeless and specifically intended to discharge metered doses of formulation.

The TEMPO inhaler is an actuator that allows for breath-synchronized drug formulation delivery from the filled canister to the patient's lungs. It automatically dispenses drug when the patient inhales and enables drug delivery to the deep lung. The inhaler discharges the metered dose of aerosol into a small integral flow control chamber (FCC). The aerosol plume is slowed in this chamber by spinning the plume into a vortex to increase residence time, and by buffeting the plume with perpendicular sidewall airflows to reduce sidewall deposition. The increased residence time allows for evaporation of the formulation propellant, leaving a high proportion of respirable drug particles in the emitted plume. The breath-synchronized trigger of the inhaler is designed to actuate the filled canister and discharge the plume within the first half of the inspiratory cycle (exchange volume), independent of peak flow rate or inspiratory volume.

The trigger and actuation assembly of the TEMPO device is comprised of various elements: the eductor, a diaphragm, a manifold, a trigger, and a cradle. Inhalation through the mouthpiece causes air flow through the inhaler. A low pressure vacuum is created at the siphon hole of the eductor by the air flowing through the element. This vacuum "pulls" on the diaphragm, which in turn causes the trigger to move. Trigger motion removes the support from the cradle, which is then free to move under the spring force. This motion causes the cradle to displace the filled canister and results in drug formulation release through the valve. The action of closing the cocking lever releases the spring compression and covers the mouthpiece.

The FCC of the TEMPO device is designed to slow and control the discharged aerosol plume of formulation. This action allows for increased residence time of the plume in the chamber, to promote evaporation of propellant and to entrain the drug particles in the inhaled airflow. The FCC is comprised of several elements: a vortex plate; the FCC backwall/atomizing nozzle; a porous tube; and the FCC front. An inhaled breath is directed through each of these elements.

The FCC vortex plate is located upstream of the atomizing nozzle. A portion of the inhalation airflow is directed through the FCC vortex plate, causing the air to flow in a rotational (vortexing) pattern. This vortex action reduces the axial speed of the particles in the airstream, increasing residence time in the FCC to allow for propellant evaporation. The vortexing pattern is achieved by a proprietary vortex plate design.

The atomizing nozzle, integrated into the FCC backwall, releases an aerosol plume into the vortexing airflow created by the vortex plate. This mixture of aerosol and air from the vortex plate is slowed by the increase in flow area within the FCC backwall/nozzle component. Inhaled air drawn through the vents of the FCC backwall/nozzle serves to (1) reduce overall flow resistance to improve patient comfort, and (2) provide sufficient axial momentum to drive the controlled, vortexing plume past the airflow entering through the FCC front and through the mouthpiece, into the patient's respiratory tract.

Air is also drawn through the porous walls of the porous tube in the TEMPO device. This flow forms a cushioning layer along the inner walls of the chamber, which inhibits deposition of aerosol on the walls. Another portion of the air pulled through the inhaler is drawn through the FCC front and is directed across the spray. This cross-flow impinging jet slows the velocity of the aerosol plume, reducing the plume velocity to approximately the same velocity as the inhalation air flow.

A cutaway depiction of a BApMDI device incorporating an enhanced eductor produced according to the present invention is depicted in FIG. 10. The Inhaler Device (500) includes an enhanced Eductor Element (510), and a Pressurized Canister (520) that includes a Primeless Valve (530). The Inhaler Device (500) is readied for use by lifting and opening a Cocking Lever (550) through an angle of approximately 135 degrees. The action of lifting the lever uncovers the Mouthpiece (540) and readies the inhaler for use. As the Cocking Lever (550) is lifted, cams on the lever compress two springs, which apply a force on a cradle holding the Pressurized Canister (520) and provide the energy to actuate the filled canister when the device is actuated. To operate the device, the patient creates a seal with his or her lips around the edge of the Mouthpiece (540) and starts to take a normal inspiratory breath. As air flow is drawn into the Inhaler Device (500) as depicted by the Arrows (A), the inspired air passes through the Enhanced Eductor (510) as depicted by the Arrow (B), and provides a siphon pressure drop that is sufficient to release the spring energy and cause the valve to discharge a dose of the aerosolized drug into a vortexing air flow depicted by the Arrow (E) which, after further vortexing in the FCC (560), exits the inhaler through the mouthpiece with the air flow depicted by Arrows (D), allowing inspiration of the drug into the patients' lungs.

EXAMPLES OF THE INVENTION

Example 1

Production of an Enhanced Eductor Element

An enhanced eductor in accordance with the present invention was produced from stock polycarbonate material using an injection molding technique. The enhanced eductor element had the following relative physical parameters:

the ratio between the height (H) of the protrusion (modification member) and the radius (R) of the constriction zone is between about 0.16 and 0.65;

the ratio between the length of the protrusion (modification member) along the eductor long axis (L) and the length of the constriction zone ($L_{CZ}$) is between 0.25 and 0.75;

the spread of the protrusion (modification member) around the perimeter of the constriction zone radius (θ) is between 60 and 120 degrees; and the reduction in the constriction zone cross-sectional area does not exceed about 21%.

In particular, on example of an enhanced eductor, "Rev003" as illustrated in FIGS. 5-6B had the following physical dimensions as set forth in Table 1 below:

TABLE 1

| Eductor Feature | Dimension |
| --- | --- |
| Overall length of the eductor ($L_E$) | 28.05 mm |
| Inlet inside diameter ($D_i$) | 6.62 mm |
| Outlet inside diameter ($D_o$) | 4.17 mm |
| centerline of siphon from inlet | 9.35 mm |
| Start of constriction zone from inlet | 5.74 mm |
| diameter of siphon at inner surface opening | 0.79 mm |
| diameter of constriction zone ($D_t$) | 2.53 mm |

TABLE 1-continued

| Eductor Feature | Dimension |
| --- | --- |
| length of constriction zone ($L_{CZ}$) | 8.66 mm |
| Modification member height (H) | 0.40 mm |
| Displacement angle of the modification member (θ) | 66 degrees |
| Length of the modification member (L) | 2.80 mm |

Example 2

Pressure Drop Generated by the Enhanced Eductor Siphon

The siphon pressure drop, and the pressure drop across the eductor for a conventional eductor (Rev 002) and an enhanced eductor element (Rev 003) produced according to the present invention was estimated using standard mathematical techniques, and then those predicted values were compared with measured values. The Rev 002 and Rev 003 eductors had identical primary eductor parameters (identical eductor lengths ($L_E$), identical inlet inside diameters ($D_i$), identical outlet inside diameters ($D_o$), identical throat diameters ($D_t$), and identical constriction zone lengths ($L_{CZ}$)). The predicted pressure drop values at various fluid flow rates for the eductors were calculated using Bernoulli's Equation:

$$\Delta P_{siphon} = (P_{Ambient} - P_{Inlet\,Apex}) = Q^2 \rho (1/A^2 - 1/a^2) 2 g_c (g_f / cm^2), \text{ where:}$$

ρ=standard temperature and pressure (STP) air density throughout=0.001193 gm/cm³;
$g_c$=gravitational constant=982.14 ($g_m/g_f$) (cm/sec²);
a=throat cross sectional area=$\pi D_t^2/4$; and
A=Inlet cross sectional area=$\pi D_i^2/4$.

The predicted pressure drop values were then compared to the measured performance of the Rev 002 and Rev 003 eductors. The results of the comparison are in Table 2, below.

thus the Δ% is small. However, for the enhanced eductor (Rev 003), Bernoulli's Equation did not accurately predict the pressure drop, and the Δ% is thus large for the majority of the flow rates. The absolute increase in the Siphon Pressure Drop for the enhanced eductor (Rev 003) is significantly larger than would have been expected or predicted based upon the current state of the art for eductor design.

Another unexpected benefit is that while the Siphon Pressure Drop was increased by effectively decreasing the constriction zone diameter in the enhanced eductor (Rev 003), the Eductor Pressure Drop did not substantially increase at comparable flow rates. This runs counter to what would be predicted by Poiseuelle's Equation, which would predict increased Eductor Pressure Drop as the protrusion of the modification member into the constriction zone narrowed its' effective diameter. The unexpected increase in Siphon Pressure Drop, with the unexpected lack of increase in the Eductor Pressure Drop is very beneficial for users of an BApMDI device employing an enhanced eductor in that it allows the user to trigger the device at lower flow rates with less effort. It has been found that the modification member protrusion can have a height as much as 0.65 times the radius of the eductor constriction zone diameter, and reduce the cross-sectional area by up to about 21% without substantially affecting the Eductor Pressure Drop (e.g., 10% or less), while increasing the Siphon Pressure Drop up to about 45% over a typical range of inhalation flow rates of 30-60 LPM.

While certain embodiments have been described herein, it will be understood by one skilled in the art that the methods, systems, and apparatus of the present disclosure may be embodied in other specific forms without departing from the spirit thereof. The present embodiments are therefore to be considered in all respects as illustrative and not restrictive of the present disclosure. Rather, the scope and spirit of the present invention is embodied by the appended claims.

TABLE 2

| | Unmodified Eductor Rev 002 | | | | Modified Eductor Rev 003 | | | |
| --- | --- | --- | --- | --- | --- | --- | --- | --- |
| Flow Rate (Liters per minute) | Measured Siphon Pressure Drop (millibars) | Bernoulli's Equation Predicted Siphon Pressure Drop (millibars) | Δ% | Eductor Pressure Drop (millibars) | Measured Siphon Pressure Drop (millibars) | Bernoulli's Equation Predicted Siphon Pressure Drop (millibars) | Δ% | Eductor Pressure Drop (millibars) |
| 10 | 8 | 8 | −1% | 5 | 10 | 10 | 6% | 4 |
| 15 | 17 | 18 | −3% | 9 | 22 | 22 | 1% | 7 |
| 20 | 31 | 32 | −4% | 16 | 40 | 39 | 1% | 12 |
| 25 | 49 | 50 | −2% | 23 | 67 | 61 | 10% | 18 |
| 30 | 71 | 72 | −1% | 31 | 100 | 88 | 12% | 26 |
| 35 | 99 | 98 | 1% | 41 | 140 | 119 | 15% | 38 |
| 40 | 133 | 128 | 4% | 53 | 191 | 156 | 19% | 50 |
| 45 | 177 | 161 | 9% | 70 | 260 | 197 | 24% | 68 |
| 50 | 232 | 199 | 14% | 96 | 351 | 243 | 31% | 93 |
| 53.2 | 280 | 226 | 19% | 128 | 469 | 275 | 41% | 126 |

The Δ% columns in Table 2 represent the percentage difference between the Bernoulli's Equation-predicted Siphon Pressure Drop and the measured Siphon Pressure Drop for the conventional eductor (Rev 002) and the enhanced eductor (Rev 003) that included a modification member per the invention. As can be seen, Bernoulli's Equation accurately predicted the pressure drop over most of the range of flow rates (10 to 53.2 LPM) for the conventional eductor (Rev 002), and

What is claimed is:

1. A breath-actuated inhalation device comprising:

(a) a medicament flow path; and (b) an enhanced eductor element comprising:

a conduit comprising an inlet, an outlet, an outer surface and an inner surface, wherein the inner surface forms a hollow bore extending from the inlet to the outlet, and the inner surface is a generally smooth continuous curvilinear surface;

the conduit further comprising a constriction zone formed by a reduction in the diameter of a portion of the hollow bore between the inlet and the outlet, wherein the constriction zone diameter is smaller than the inlet diameter and the outlet diameter, and wherein the constriction zone has a length ($L_{CZ}$) along the main axis of the eductor, and a radius (R);

a modification member disposed upon the conduit inner surface and in the constriction zone, wherein the modification member is a protrusion that locally reduces the constriction zone diameter and cross-sectional area, and wherein the modification member has a length (L) along the main axis of the eductor, and a height (H); and a siphon channel which establishes fluid communication between the conduit outer surface and the conduit inner surface, wherein the channel is adjacent to or surrounded by the modification member;

wherein the eductor element increases the local velocity of the flow of an inspiratory breath to actuate the breath-actuated inhalation device; and wherein the conduit is not positioned within the medicament flow path.

2. The device of claim 1, wherein the modification member height (H) does not exceed 0.65 times the constriction zone radius (R).

3. The device of claim 2, wherein the ratio of the modification member height (H) to the constriction zone radius (R) is about 0.16 to about 0.55.

4. The device of claim 1, wherein the modification member length (L) does not exceed 0.75 times the constriction zone length ($L_{CZ}$).

5. The device of claim 4, wherein the ratio of the modification member length (L) to the constriction zone length ($L_{CZ}$) is between about 0.25 and about 0.75.

6. The device of claim 1, wherein the ratio of the modification member length (L) to the constriction zone radius (R) is about 1.2 to about 3.0.

7. The device of claim 1, wherein the modification member decreases the cross-sectional area of the constriction zone by 21% or less.

8. The device of claim 1, wherein the spread of the protrusion of the modification member around the perimeter of the constriction zone radius (R) is between 60 and 120 degrees.

9. The device of claim 1, further comprising an actuation assembly including the enhanced eductor element.

10. The device of claim 9, wherein air flowing through the eductor element with the inspiratory breath creates a low pressure drop at the siphon channel that actuates the device.

11. The device of claim 1, wherein said device is a pressurized metered dose inhaler.

12. The device of claim 1, further comprising a pressurized canister containing an aerosol formulation of drug particles, wherein the canister further comprises a primeless valve for release of the aerosolized drug into the device upon actuation of the device.

13. The device of claim 12, wherein the pressurized canister comprises a point of discharge for releasing the aerosolized drug into the primeless valve.

14. The device of claim 13, further comprising a mouthpiece for inhalation by a patient, said mouthpiece having an outlet with an edge.

15. The device of claim 14, wherein the medicament flow path begins at the pressurized canister point of discharge and terminates at the mouthpiece outlet edge.

16. The device of claim 15, wherein the activation of the device discharges a dose of the aerosolized drug, such that the drug exits the device through the mouthpiece outlet, allowing inspiration of the drug into the patient's lungs.

17. The device of claim 1, wherein the modification member increases siphon pressure drop as a function of flow rate without significantly increasing pressure drop across the enhanced eductor element.

18. The device of claim 1, wherein the channel is adjacent to the modification member.

19. The device of claim 1, wherein the channel is surrounded by the modification member.

* * * * *